United States Patent [19]

Gammill

[11] 4,412,071

[45] Oct. 25, 1983

[54] ANTIATHEROSCLEROTIC COMPOSITIONS

[75] Inventor: Ronald B. Gammill, Portage, Mich.

[73] Assignee: The Upjohn Company, Kalamazoo, Mich.

[21] Appl. No.: 378,702

[22] Filed: May 17, 1982

[51] Int. Cl.[3] ................ C07D 491/048; C07D 498/04

[52] U.S. Cl. ................ 544/58.6; 260/243.3; 424/246; 424/248.5; 424/248.51; 424/248.52; 424/248.56; 424/248.57; 424/248.58; 424/250; 544/71; 544/73; 544/95; 544/231; 544/234; 549/387; 549/470; 549/471; 549/486

[58] Field of Search ................ 544/95, 234, 58.6, 71, 544/73, 231; 260/243.3

[56] References Cited

U.S. PATENT DOCUMENTS

| | | | |
|---|---|---|---|
| 2,680,119 | 6/1954 | Robertson et al. | 260/345.2 |
| 4,284,569 | 8/1981 | Gammill | 260/345.2 |

OTHER PUBLICATIONS

Abu-Shady, H., Experiments with Khellin VII., UAR J. Pharm. Sci., 11:283-288 (1970).

Abu-Shady, H., et al., Experiments with Khellin-VIII, J. Pharm. Belg., 33:397-399 (1978).

Anrep, G. V. et al., Therapeutic Uses of Khellin, The Lancet, pp. 557-558, Apr. 26, 1947.

Anrep, G. V. et al., The Coronary Vasodilator Action of Khellin, Amer. Heart J., 37:531-542 (1949).

Apffel, C. A., Die Zytostatische Wirkung von Chinonen und Ihren Derivaten, Deut. Med. Wochschr., 80:414-416 (1955).

Aubertin, E., La Khelline, agent de relachement de la musculature lisse., J. Med. Bordeaux, 127:821-823 (1950).

Baytop, O. T., Khellin'in Yer Solucanlarina Tesiri Hakkinda, Folia Pharm. (Turkey), 1:48-49 (1949).

Best, M. M. et al., Effects of Dioxyline Phosphate and Enteric-Coated Khellin on Coronary Artery Insufficiency, Amer. J. Med. Sci. 222:35-39 (1951).

Chen, G. et al., The Central Nervous Depressive Effect of Khellin, Proc. Soc. Expetl. Biol. Med., 78:305-307 (1951).

Columbo, G. et al., Sulla attivita di alcune sostanze del gruppo della Kellina sulla motilita ureterale—in vitro—, Arch. Sci. Med. 97:71-81 (1954).

Day, C. E. et al., Utility of a Selected Line (SEA) of the Japanese Quail for the Discovery of New Anti-Atherosclerosis Drugs, Laboratory Animal Science, 27:817-821 (1977).

Eaton, R. P., High Density Lipoprotein—Key to Anti-Atherogenesis, J. Chron. Dis., 31:131-135 (1978).

Haust, M. D., Reaction Patterns of Intimal Mesenchyme to Injury, and Repair in Atherosclerosis, Adv. Exp. Med. Biol., 43:35-57 (1974).

Huttrer, C. P. et al., The Chemistry and Physiological Action of Khellin and Related Products, Chem. Revs., 48:543-579 (1951).

Jordan, H., Cardiovasculare Wirkungen Intravenoser Khellin-Injektionen, Arzneimittel-Forsch 8:141-143 (1958), 7:82-85 (1957).

LaBarre, J. et al., Action protectrice de la khelline vis-a-vis de pulcere gastrique experimental provoque, chez le chien, par l'administration de cinchophene, Compt. Rend. Soc. Biol., 150:598-599 (1956).

LaBarre, J. et al., A propos de l'action inhibitrice de la khelline dans l'ulcere gastrique experimental provoque par administration journaliere de phenylbutazone, Compt. Rend. Soc. Biol., 150:1806-1807 (1956).

Lian, C. et al., Etude Experimentale et Clinique de la Khelline, Acta. Cardiol. (Brussels), 5:373-388 (1950).

Montorsi, W. et al., Sur L'Activite de Certaines Substances du Groupe de la Khelline, Presse Med., 63:81 (1955).

Musante, C. et al., Furil E. Isossazol-Furo-Cromoni e Derivati, Pharmaco, (Pavie) Ed Sci., 15:81-94 (1960).

Mustafa, A. et al., Experiments with Furochromones, Synthesis of Ammiol and Khellol, J. Org., Chem., 26:886-890 (1961).

Mustafa, A., Furopyrans and Furopyrones, John Wiley and Sons, Inc., NY (1967), pp. 102-159 (Chapter III: Furochromones).

Osher, H. L., et al., Khellin in the Treatment of Angina Pectoris, New England J. Med., 244:315-321 (1951).

Raymond-Hamet, M., Compt. Rend., 238:1624-1626 (1954).

Samaan, K. et al., The Response of the Heart to Visammin and to Khellinin, J. Pharm. Pharmacol., 1:538-544 (1949).

Samaan, K. et al., The Existence in Ammi Visnaga of a Cardiac Depressant Principle Visammin and a Cardiac Stimulant Glycoside Khellinin, J. Roy. Egypt Med. Assoc., 33:953-960 (1950).

Schonberg, A. et al., Khellin and Allied Compounds, JACS 72:1611-1617 (1950).

Schonberg et al., Furo-Chromones and -Coumarins, XIV, JACS 77:5439-5440 (1955).

Schurr, P. E., High Volume Screening Procedure for Hypobetalipoproteinemia Activity in Rats, Adv. Exp. Med. Biol. 67: Atherosclerotic Drug Discovery, pp. 215-229, Plenum Press (1975).

Silber, E. N., The Effect of Khellin on Cardio-Pulmonary Function in Chronic Pulmonary Disease, published in 1951.

Swayne, V. R. et al., Spermicidal Action of Khellin, Amer. J. Pharm., 125:295-298 (1953).

*Primary Examiner*—Richard Raymond
*Attorney, Agent, or Firm*—Robert A. Armitage

[57] ABSTRACT

The present invention provides novel antiatherosclerotic furobenzoxazinones, e.g., 4,9-dimethoxy-4H-furo[3,2-g][1,3]benzoxazin-4-ones. These compounds are structurally and pharmacologically related to khellin and are useful antiatherosclerotic agents.

7 Claims, No Drawings

ANTIATHEROSCLEROTIC COMPOSITIONS

DESCRIPTION

BACKGROUND OF THE INVENTION

The present specification provides novel compositions of matter and novel methods of their preparation.

The present specification particularly relates to novel analogs of a known pharmacological agent, khellin, also known as "visamin", and structurally related antiatherogenic furochromones and other benzopyrans. Chemically, khellin is a furochromone. Furochromones are characterized generally by the structural formula IV. Specifically, khellin is the furochromone of formula V, and is trivially named 7-methyl-4,9-dimethoxyfurochromone. Khellin and related furochromones are naturally-occurring substances and have been used in crude form as pharmacological agents for centuries. Khellin is an extract from the plant Ammi visnaga. This plant grows wild in Eastern Mediterranean countries. Aside from khellin, Ammi visnaga is also a source of at least three other known and characterized furochromones, specifically visnagin, khellinin, and ammiol.

As indicated above, khellin exhibits a wide variety of pharmacological actions, rendering this compound a useful agent for numerous pharmacological purposes. For a comprehensive, but somewhat dated, review of the chemistry and physiological action of khellin-related products, see the reports of Huttrer, C. P., et al., Chem. Revs. 48:543-79 (1951) and Aubertin, E., J. Med. Bordeaux 127:821-823 (1950).

One principal action of khellin is its ability to induce relaxation of smooth muscle tissues. Particularly, khellin is known as a potent dilator of coronary blood vessels. This potent coronary vasodilator activity of khellin renders the compound useful in the treatment of angina pectoris and other diseases characterized by coronary artery insufficiency. For a description of the use of khellin in the treatment of such diseases, see Osher, H. L., et al., "Khellin in the Treatment of Angina Pectoris", The New England Journal of Medicine 244:315 (1951). Also the effects of enteric-coated khellin on coronary artery insufficiency is reported by Best, M. M., et al., J. Med. Sci. 222:35-9 (1951). The ability of khellin to relax smooth muscle also extends to gastrointestinal smooth muscle where khellin has been administered to inhibit peristalsis, thus indicating antidiarrhetic potential. See Raymond-Hamet, M., Compt. Rend. 238:1624-6 (1954). Khellin may also be useful for the treatment of gastrointestinal disorders exhibiting a spasmotic component, as suggested by Anrep, G. V., et al., Amer. Heart J. 37:531-542 (1949). Further the antispasmotic effects of khellin on the urethra is reported by Colombo, G., et al., Arch. Sci. Med. 97:71 (1954) and Montersi, W., et al., Presse Med. 63:81 (1955).

The antispasmotic action of khellin also extends to bronchial smooth muscle, rendering khellin useful in the treatment of asthma and other hypoxic pulmonary diseases. In this regard, see Silber, E. N., et al., "The Effect of Khellin on Cardio-Pulmonary Function in Chronic Pulmonary Disease", published in 1951; Anrep. G. V., et al., "Therapeutic Uses of Khellin", The Lancet, Apr. 26, 1947, pages 557-8.

Khellin has also been reported to exert a hypotensive effect in humans by Jordan, H., Arzneimittel-Forsch 8:141-3 (1958), and 7:82-5 (1957). An additional account of the hypotensive effect of khellin is provided by Lian, C., et al., Acta. Cardiol. (Brussels) 5:373-88 (1950). With respect to overall cardiac effects, however, khellin has been reported to exert a cardiac depressive activity. In this regard see Samaan, K., et al., J. Roy. Egypt Med. Assoc. 33:953 (1950) and J. Pharm. Pharmacol. 1:538-44 (1949).

In addition to its effect on gastrointestinal smooth muscle reported above, khellin is also known as a gastric antisecretory and antiulcer agent. In this regard, the gastric antisecretory activity of khellin is reported by LaBarre, J., Compt. Rend. Soc. Biol. 150:1806-7 (1956) and 150:598-9 (1956).

Numerous other miscellaneous properties of khellin are also reported. For an account of its anthelminic activity see Baytop, O. T., Folia, Pharm. (Turkey) 1:48-9 (1949). For an account of the CNS depressant activity of khellin see Chen, G., Proc. Soc. Expetl. Biol. Med. 78:305-7 (1951). For an account of the cytostatic activity of khellin see Apffel, C. A., Deut. Med. Wochschr. 80:414-16 (1955). Finally, the spermacidal action of khellin is reported by Swayne, V. R., et al., Amer. J. Pharm. 125:295-8 (1953).

Khellin and numerous chemically related furochromones (and derivatives thereof) are also useful in treatment and prevention of atherosclerosis by methods described in U.S. Pat. No. 4,284,569.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hyperalpha-lipoproteinemic activity) is postulated to have direct antiatherosclerotic effects. See Eaton, R. P., J. Chron. Dis. 31:131-135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis:, Adv. Exp. Med. Biol. 43:35-37 (1974), which postulates that serum LDL is a factor in atherosclerotic lesion formation.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rat model, refer to the known methods of Schurr, P. E., et al., "High Volume Screening Procedure for Hypobetalipoproteinemia Activity in Rats", Adv. Exp. Med. Biol. 67: Atherosclerotic Drug Discovery, pp. 215–229, Plenum Press (1975). For a description of the Japanese quail model, see Day, C. E., et al., "Utility of a Selected Line (SEA) of the Japanese Quail (Coturnic Coturnix japonica) for the Discovery of New Anti-Atherosclerosis Drugs", Laboratory Animal Science 27:817–821 (1977).

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

The khellin, the khellin-related products of Ammi visnaga, and related furochromones (and derivatives) described in U.S. Pat. No. 4,284,569 are all characterized by pronounced antiatherogenic activity, rendering these compounds useful in the treatment and prophylaxis of atheroscherosis, atherogenic hyperlipoproteinemia (i.e., hypobetalipoproteinemia) and atherogenic hypolipoproteinemia (i.e., hypoalphalipoproteinemia), and the untoward consequences thereof. These compounds exhibit this useful pharmacological activity in both mammalian and non-mammalian species, including humans.

The patients susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Patients manifesting two or more risk factors are deemed to be especially susceptible to atherosclerotic diseases. These khellin-related materials all exhibit pronounced oral pharmacologic activity. Accordingly, in using these compounds for the treatment of atherosclerosis, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

In humans, the preferred route of administration is oral, in the form of capsules or tablets containing the drug.

The patient or animal being treated must be given periodic doses of the drug in amounts effective to reduce atherogenic serum lipoproteins (e.g., betalipoproteins) or selectively enhance levels of antiatherogenic serum lipoproteins (e.g. enhancing alphalipoprotein levels, while suppressing, or at least unaffecting, betalipoprotein levels). Such effective dosages are readily determined by methods known in the art. For example, small daily doses of the drug (e.g., 50–100 mg) may be administered initially with higher succeeding doses until levels of atherogenic or antiatherogenic serum lipoproteins are favorably affected. By this regimen, a compound is administered initially at doses as low as about 50 mg per patient per day, with increasing doses up to about 200 mg per patient per day. In the event the antiatherogenic response in a patient being treated at a dose of 200 mg per day is insufficient, higher doses are also utilized to the extent patient tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily dosages of drug are to be administered, each such dose may be about 50 mg per patient per dose (200–300 mg per patient per dose), or higher depending on tolerance.

Similar doses are employed in non-human mammals, e.g., 1–5 mg/kg/day.

4,9-Dimethoxyfurochromones are known in the art. Such known compounds include 7-ethyl, 7-phenyl, 7-propyl, and 7-ethoxycarbonyl analogs described by Schonberg, A., et al., JACS 72:1611–17 (1950); 7-γ-pyridyl analogs, described by Schonberg, A., JACS 77:5439 (1955); 7-furanyl analogs, described by Musante, C., et al., Pharmaco. (Pavie) Ed. Sci. 15:81–94 (1960); 7-carboxyaldehyde analogs, described by Mustafa, A., et al., J. Org. Chem. 26:886 (1961). Also, 6-substituted-4,9-dimethoxyfurochromones are known. See, for example, the compounds described by Abu-Shady, H.) UAR J. Pharm. Sci. 11:283 (1970).

4-Methoxy-7-aminomethylenefurochromones are also known in the art. See Abu-Shady, H., et al, J. Pharm. Belg. 33:397 (1978).

A wide variety of antiatherosclerotic furochromones are described in U.S. Pat. No. 4,284,569.

PRIOR ART

Extensive pharmacological uses for khellin and related substances are known, as indicated above. Khellin analogs are also known in the art, as indicated above. See especially U.S. Pat. No. 4,284,569 and the review by Mustafa, A., "Furopyrans and Furopyrones," John Wiley and Sons, Inc., N.Y., N.Y. (1967), pp. 102–159 (Chapter III: Furochromones). Also see U.S. Pat. No. 2,680,119 describing 6- and/or 7-substituted furochromones, i.e., alkyl, alkoxyalkyl and phenylalkyl substituted compounds.

SUMMARY OF THE INVENTION

The present invention particularly provides:

(1) An antiatherosclerotic furochromone of formula I, II, or III wherein W is oxo (=O) or α-$R_1$:β-$R_2$, wherein $R_1$ and $R_2$, being the same or different, are individually:

(a) $C_1$–$C_6$ alkyl,
(b) trifluoromethyl,
(c) $C_5$–$C_{10}$ cycloalkyl with the proviso that the cycloalkyl ring is $C_5$–$C_7$,
(d) $C_2$–$C_8$ alkoxyaminoalkyl,
(e) $C_2$–$C_8$ alkoxyalkyl,
(f) $C_2$–$C_8$ alkylthioalkyl,
(g) $C_2$–$C_8$ alkylsulfinylalkyl,
(h) $C_2$–$C_8$ alkylsulfonylalkyl,
(i) $C_7$–$C_{12}$ phenoxyalkyl optionally substituted on the phenyl ring by one, 2, or 3,
(i) hydroxy,
(ii) $C_1$–$C_3$ alkoxy,
(iii) $C_1$–$C_3$ alkyl,
(iv) trifluoromethyl, (v) halo which is fluoro, chloro, or bromo, with the proviso that not more than two such substituents are other than alkyl,
(j) $C_7$-$C_{12}$ phenylthioalkyl optionally substituted on the phenyl ring by one, 2 or 3,
(i) hydroxy,
(ii) $C_1$-$C_3$ alkoxy,
(iii) $C_1$-$C_3$ alkyl,
(iv) trifluoromethyl,
(v) halo which is fluoro, chloro, or bromo, with the proviso that not more than two such substituents are other than alkyl,
(k) phenyl optionally substituted by one, 2, or 3,
(i) hydroxy,
(ii) $C_1$-$C_3$ alkoxy,
(iii) $C_1$-$C_3$ alkyl,
(iv) trifluoromethyl,
(v) halo which is fluoro, chloro, or bromo, with the proviso that not more than two such substituents are other than alkyl,
(l) aralkyl optionally substituted on the aromatic ring by one, 2, or 3,
(i) hydroxy,
(ii) $C_1$-$C_3$ alkoxy,
(iii) $C_1$-$C_3$ alkyl,
(iv) trifluoromethyl,
(v) halo which is fluoro, chloro, or bromo, with the proviso that not more than two such substituents are other than alkyl,
(m) 2- or 3-furanyl optionally substituted by
(i) hydroxy,
(ii) $C_1$-$C_3$ alkoxy,
(iii) $C_1$-$C_3$ alkyl,
(iv) trifluoromethyl,
(v) halo which is fluoro, chloro, or bromo, with the proviso that not more than two such substituents are other than alkyl,
(n) 2- or 3-thenyl optionally substituted by
(i) hydroxy,
(ii) $C_1$-$C_3$ alkoxy,
(iii) $C_1$-$C_3$ alkyl,
(iv) trifluoromethyl,
(v) halo which is fluoro, chloro, or bromo, with the proviso that not more than two such substituents are other than alkyl, or
(o) $-(CH_2)_pNR_{10}R_{11}$ wherein p is one, 2, or 3, and $R_{10}$ and $R_{11}$, being the same or different, are individually,
(i) hydrogen,
(ii) $C_1$-$C_8$ alkyl,
(iii) $C_5$-$C_{10}$ cycloalkyl,
(iv) $C_7$-$C_{12}$ aralkyl, or
(v) phenyl optionally substituted by one, 2, or 3
(a) hydroxy,
(b) $C_1$-$C_3$ alkoxy,
(c) $C_1$-$C_3$ alkyl,
(d) trifluoromethyl,
(e) halo which is fluoro, chloro, or bromo, with the proviso that not more than two such substituents are other than alkyl, or wherein $R_{10}$ and $R_{11}$ are taken together with the nitrogen to form a saturated or unsaturated heterocylic amine ring consisting of from 2 to 7 carbon atoms, inclusive, and zero, one, or 2 additional hetero atoms or hetero atom groups, with the proviso that said heterocyclic amine ring contains 4 to 8 atoms in the ring, said additional hetero atoms or hetero atom groups being selected from the group consisting of oxygen, nitrogen, sulfur, —SO—, and —$SO_2$— said heterocyclic amine ring being optionally substituted by one or 2 $C_1$-$C_4$ alkyl, $C_2$-$C_8$ alkylthiomethyl, or $C_2$-$C_8$ alkoxymethyl, $C_1$-$C_4$ hydroxyalkyl or phenyl; or wherein $R_1$ and $R_2$ are taken together and form a bivalent moiety which is:
(a) —$CH_2$—$(CH_2)_a$—$CH_2$— wherein the integer "a" is zero to 5;
(b) —$CH_2$—$(CH_2)_b$—X—$(CH_2)_c$—$CH_2$— wherein the integer "b" is zero and the integer "c" is zero, one, 2, or 3 or the integer "b" is one and the integer "c" is zero, one, or 2, and wherein X is oxa (—O—), thia (—S—), or —$N(R_{10})$— wherein $R_{10}$ is
(i) hydrogen,
(ii) $C_1$-$C_8$ alkyl,
(iii) $C_5$-$C_{10}$ cycloalkyl,
(iv) $C_7$-$C_{12}$ aralkyl, or
(v) phenyl optionally substituted by one, 2, or 3
(a) hydroxy,
(b) $C_1$-$C_3$ alkoxy,
(c) $C_1$-$C_3$ alkyl,
(d) trifluoromethyl,
(e) halo which is fluoro, chloro, or bromo, with the proviso that not more than two such substituents are other than alkyl;

wherein $R_3$ is hydrogen, or $C_1$-$C_4$ alkoxy and $R_4$ is hydrogen or $C_1$-$C_4$ alkoxy, with the proviso that one of $R_3$ and $R_4$ is hydrogen only when the other is other than hydrogen; and wherein $R_8$ and $R_9$ being the same or different, are individually,
(i) hydrogen,
(ii) $C_1$-$C_8$ alkyl,
(iii) $C_5$-$C_{10}$ cycloalkyl,
(iv) $C_7$-$C_{12}$ aralkyl, or
(v) phenyl optionally substituted by one, 2, or 3
(a) hydroxy,
(b) $C_1$-$C_3$ alkoxy,
(c) $C_1$-$C_3$ alkyl,
(d) trifluoromethyl,
(e) halo which is fluoro, chloro, or bromo, with the proviso that not more than two such substituents are other than alkyl, or wherein $R_8$ and $R_9$ are taken together with the nitrogen to form a saturated or unsaturated heterocyclic amine ring consisting of from 2 to 7 carbon atoms, inclusive, and zero, one, or 2 additional hetero atoms or hetero atom groups, with the proviso that said heterocyclic amine ring contains 4 to 8 atoms in the ring, said additional hetero atoms or hetero atom groups being selected from the group consisting of oxygen, nitrogen, sulfur, —SO—, and —$SO_2$— said heterocyclic amine ring being optionally substituted by one or 2 $C_1$-$C_4$ alkyl, $C_2$-$C_8$ alkylthiomethyl, or $C_2$-$C_8$ alkoxymethyl, $C_1$-$C_4$ hydroxyalkyl or phenyl.

(2) An antiatherosclerotic furochromone of formula I;

(3) An antiatherosclerotic furochromone selected from the group consisting of:
(a) 5,9-Dimethoxy-2-(1-pyrrolidinyl)-4H-furo[3,2-g][1,3benzoxazin-4-one;
(b) 5,9-Dimethoxy-2-(4-morpholinyl)-4H-furo[3,2-g][1,3]benzoxazin-4-one;
(c) 5,9-Dimethoxy-2-K(N,N-dimethylamino)-4H-furo[3,2-g][1,3]benzoxazin-4-one;
(d) 2-[2-(Hydroxymethyl)-1-pyrrolidinyl]-5,9-dimethoxy-4H-furo[3,2-g][1,3]benzoxazin-4-one;

(e) 5,9-Dimethoxy-2-(4-methyl-1-piperazinyl)-4H-furo[3,2-g]benzoxazin-4-one;
(f) 5,9-Dimethoxy-2-(tetrahydro-4H-1,4-thiazin-4-yl)-4H-furo[3,2-g][1,3]benzoxazin-4-one;
(g) 2-[[2-(Diethylamino)-ethyl]ethylamino]-5,9-dimethoxy-4H-furo[3,2-g][1,3]benzoxazin-4-one;
(h) 5,9-Dimethoxy-2-(3-thiazolidinyl)-4H-furo[3,2-g][1,3]benzoxazin-4-one;
(i) 2-[[(2S)-6,6-Dimethyl-(bicyclo[3.1.1]hept-2-yl)methyl]amino]-5,9-dimethoxy-4H-furo[3,2-g][1,3]benzoxazin-4-one; and
(j) 2-(2,6-Dimethyl-4-morpholinyl)-5,9-dimethoxy-4H-furo[3,2-g][1,3]benzoxazin-4-one.

(4) An antiatherosclerotic compound of formula II.

(5) An antiatherosclerotic compound selected from the group consisting of:
(a) 5,9-Dimethoxy-4H-furo[3,2-g][1,3]benzoxazine-2,4-dione;
(b) 2′,3′,5′,6′-Tetrahydro-5,9-dimethoxy-spiro[2H-furo[3,2-g][1,3]benzoxazine-2,4′-[4H]thiopyran]-4(3H)-one;
(c) 5′,9′-Dimethoxy-spiro[cyclohexane-1,2′-[2H]furo[3,2-g][1,3]benzoxazin-4′(3′H)-one;
(d) 2,2-Diethyl-2,3-dihydro-5,9-dimethoxy-4H-furo[3,2-g][1,3]benzoxazin-4-one; and
(e) 2,3-Dihydro-5,9-dimethoxy-2-methyl-2-[(methylthio)methyl]-4H-furo[3,2-g][1,3]benzoxazin-4-one.

(6) An antiatherosclerotic compound of formula III; and (7) 4,9-Dimethoxyfuro[3,2-g]phthalazin-5(6H)-one, an antiatherosclerotic compound according to claim 6.

The carbon atom content of various hydrocarbon containing moieties is indicated by a prefix designating the minimum and maximum number of carbon atoms in the moiety, i.e., the prefix $C_i$–$C_j$ indicates a carbon atom content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the above, $C_1$–$C_4$ alkyl is methyl, ethyl, propyl, or butyl, including isomeric forms thereof. Similarly, $C_1$–$C_6$ alkyl is methyl, ethyl, propyl, butyl, pentyl, hexyl, and isomeric forms thereof.

Examples of cycloalkyl of 3 to 10 carbon atoms, inclusive, are cyclopropyl, cyclobutyl, cyclopentyl, cyclohexyl, cycloheptyl, cyclodecyl, cyclopropylmethyl, cyclobutylmethyl, cyclopentylmethyl, cyclohexylmethyl, cycloheptylmethyl, 1- or 2-cyclopropylethyl, 1- or 2-cyclobutylethyl, 1- or 2-cyclopentylethyl, 1- or 2-cyclohexylethyl, 1-, 2-, 3- or 4-methylcyclohexyl, (bicyclo[3.1.1]hept-2-yl)methyl, and 6,6-dimethyl-(bicyclo[3.1.1]hept-2-yl)methyl.

Example of alkoxyaminoalkyl are methylaminomethyl, ethylaminomethyl, propylaminomethyl, butylaminomethyl, isopropylaminomethyl, isobutylaminomethyl, tert-butylaminomethyl, pentylaminomethyl, and n-hexylaminomethyl.

Examples of $C_2$–$C_8$ alkoxyalkyl are methoxymethyl, ethoxymethyl, propoxymethyl, butoxymethyl, pentoxymethyl, hexoxymethyl, and heptoxymethyl.

Examples of $C_2$–$C_8$ alkylthioalkyl are methylthiomethyl, ethylthiomethyl, propylthiomethyl, butylthiomethyl, isopropylthiomethyl, isobutylthiomethyl, tert-butylthiomethyl, pentylthiomethyl, and n-hexylthiomethyl.

Examples of $C_2$–$C_8$ alkylsulfinylalkyl are methylsulfinylmethyl, ethylsulfinylmethyl, propylsulfinylmethyl, butylsulfinylmethyl, isopropylsulfinylmethyl, isobutylsulfinylmethyl, tert-butylsulfinylmethyl, pentylsulfinylmethyl, and n-hexylsulfinylmethyl.

Examples of $C_2$–$C_8$ alkylsulfonylalkyl are methylsulfonylmethyl, ethylsulfonylmethyl, propylsulfonylmethyl, butylsulfonylmethyl, isopropylsulfonylmethyl, isobutylsulfonylmethyl, tert-butylsulfonylmethyl, pentylsulfonylmethyl, and n-hexylsulfonylmethyl.

Example of $C_6$–$C_{12}$ phenoxyalkyl optionally substituted are phenoxymethyl, phenoxyethyl, phenoxypropyl, phenoxybutyl, phenoxypentyl, 1-, 2-, or 3-methylphenoxymethyl, 1-, 2-, or 3-hydroxyphenoxymethyl, 1-, 2-, or 3-methoxyphenoxymethyl, 1-, 2-, or 3-trifluoromethylphenoxymethyl, 1-, 2-, or 3-fluorophenoxymethyl, and 1-fluoro-3-methyl-phenoxymethyl.

Example of $C_6$–$C_{12}$ phenylthioalkyl optionally substituted are phenylthiomethyl, phenylthioethyl, phenylthiopropyl, phenylthiobutyl, phenylthiopentyl, 1-, 2-, or 3-methylphenylthiomethyl, 1-, 2-, or 3-hydroxyphenylthiomethyl, 1-, 2-, or 3-methoxyphenylthiomethyl, 1-, 2-, or 3-trifluoromethylphenylthiomethyl, 1-, 2-, or 3-fluorophenylthiomethyl, and 1-fluoro-3-methyl-phenylthiomethyl.

Example of $C_6$–$C_{12}$ phenyl optionally substituted are phenyl, 1-, 2-, or 3-methylphenyl, 1-, 2-, or 3-hydroxyphenyl, 1-, 2-, or 3-methoxyphenyl, 1-, 2-, or 3-trifluoromethylphenyl, 1-, 2-, or 3-fluorophenyl, and 1-fluoro-3-methylphenyl.

Examples of aralkyl of 7 to 12 carbon atoms are naphthylmethyl and haphthylethyl.

Examples of heterocyclic amines corresponding to heterocyclic amine rings are thiazolidine, 3-piperidine methanol, 2-piperidine methanol, piperidinic acid, 3-piperidine ethanol, 2-piperidine ethanol, 1-piperizine-propanol, p-piperazinoacetoxyphenone, 4-phenyl-1,2,3,6-tetrahydropyridine, 4-phenylpiperidine, proline, 3-pyrolidinol, tetrahydrofurfurylamine, pyrrolidimethanol, 3-pyrroline, thiazolidine-4-carboxylic acid, thiomorpholine, nipecstamide, morpholine, 2-methylpiperidine, 3-methylpiperidine, 4-methylpiperidine, N-methylpiperazine, and 1-methylhomopiperazine.

The compounds in accordance with the present invention are all useful as antiatherosclerotic agents. Thus these compounds are employed by methods known in the art for the use of khellin and related furochromones in the treatment and prevention of atherosclerosis. Accordingly, compounds of formula I are employed in humans and in nonhuman mammals at doses from about 0.1–50 mg/kg/day orally. These compounds are used orally in conventional oral dosage forms, including capsules, tablets, and pharmaceutically acceptable liquids. Other routes of administration may also be employed, utilizing equivalent dosages and the appropriate conventional dosage form for the route of administration selected. Such alternatively dosage forms include rectal, vaginal, subcutaneous, intravenous, and like routes of administration.

The preparation of the novel antiatherosclerotic compounds of formulas I–III are described by the charts herein. With respect to these charts, $R_1$, $R_2$, $R_3$, $R_4$, $R_8$ and $R_9$ are as defined above. $R_5$ is $C_1$–$C_4$ alkyl.

The compounds of formulas I, II, or III each exhibit a nitrogen-containing tricyclic ring structure. By virtue of this ring structure, the compounds of formula I are all named as 5-alkoxy-, 9-alkoxy-, or 5,9-dialkoxy-4H-furo[3,2-g][1,3]benzoxazin-4-ones. Similarly, compounds of formula II are all named as 5,9-dialkoxy-2,3-dihydro-4H-furo[3,2-g][1,3]benzoxazin-4-ones. When the group W in formula II is oxo, the compounds so described are 5-alkoxy-, 9-alkoxy-, or 5,9-dialkoxy-4H-furo[3,2-g][1,3]benzoxazines-2,4-diones. Finally, formula III compounds are named as 4-alkoxy-, 5-alkoxy-, or 4,9-dialkoxy-furo[3,2-g]phthalazin-5(6H)-ones.

With respect to Chart A, a method is provided whereby the formula XXI intermediate is transformed to the novel formula XXIII and formula XXIV antiatherosclerotic furochromone in accordance with the present specification. The formula XXI compound is known in the art, or prepared by methods known in the art.

Preferably, the formula XXI compound is prepared by the methods described in Appendix A.

The formula XXII cyanoether is then prepared from the formula XXI compound by treatment with cyanogen bromide. This reaction proceeds readily in acetone employing a catalytic amount of a tertiary amine base, e.g., triethylamine. Thereafter, the formula XXIII products are prepared from the formula XXII compound employing the amine ($NHR_8R_9$) corresponding to the formula XXIII product in acetonitrile.

The formula XXIV product is then prepared from the formula XXIII compound wherein $R_8$ and $R_9$ are both hydrogen by hydrolysis. This hydrolysis proceeds readily under acetic conditions, for example, utilizing an aqueous mineral acid (hydrochloric acid) in a solvent, e.g., methanol.

Chart B provides a method whereby the formula XXXI compound, referred to as the formula XXI compound in Chart A, is transformed to the formula XXXIV antiatherosclerotic products. In accordance with the procedure of Chart A, the formula XXXI ester is first converted to the corresponding amide by conventional means. For example, the formula XXXI compound is preferably treated with saturated aqueous ammonia at elevated temperatures. Thereafter, the formula XXXII compound is converted to the formula XXXIV products by reaction with the formula XXXIII ketone. In accomplishing this transformation, the formula XXXII and formula XXXIII reactants are combined at elevated temperature in a suitable organic solvent (e.g., benzene or toluene) with a catalytic amount of amine base (e.g., pyrrolidine). The formula XXXIV product is then recovered over a reaction time ranging from several hours to several days.

The resulting formula XXXIV product is then recovered by conventional means, e.g., filtration, chromatography, and crystallization.

Chart C provides a method whereby the formula XLIII antiatheroschlerotic products are prepared from the formula XLI reactant. The formula XLI reactant is known in the art or prepared by methods known in the art. Preferably, the formula XLI reactant is prepared by methods described in Appendix A.

In accordance with the procedure of Chart C, the formula XLI compound is reacted with hydrazine to yield the formula XLIII product. This reaction proceeds in an organic solvent in the absence of water (e.g., ethanol) at elevated temperature.

The novel products of the present invention which are sulfoxides or sulfones are prepared from products herein which are the corresponding thio compounds by oxidization with either one or two equivalents, respectively, of an appropriate oxidizing agent. Appropriate oxidizing agents for this purpose include m-chloroperoxybenzoic acid and sodium periodate.

In accordance with the procedures of the present invention, there are thus prepared the various novel antiatherosclerotic products of the present disclosure.

DESCRIPTION OF THE PREFERRED EMBODIMENTS

The present invention is more completely understood by the operation of the following examples:

EXAMPLE 1

4,7-Dimethoxy-6-cyanooxy-5-benzofurancarboxylic acid methyl ester (Formula XXII: $R_3$ and $R_4$ are both methoxy and $R_5$ is methyl)

Refer to Chart A.

6-Hydroxy-4,7-dimethoxy-5-benzofurancarboxylic acid, methyl ester (18.0 g) and cyanogen bromide, BrCN (8.2 g), are added to acetone (200 ml) and cooled to 0° C. To the resulting solution is added triethylamine (7.8 g) in acetone (15 ml). The reaction is stirred for one hour and then filtered to remove triethylamine hydrobromide. The filtrate is then concentrated under reduced pressure to yield title product as an off-white solid. Washing with 20% diethyl ether and hexane followed by filtration yields 15.35 g of pure title product, melting point 95°-96° C. Silica gel TLC $R_f$ is 0.8 in 10% ethyl acetate in trichloromethane. IR absorptions ($cm^{-1}$) are observed at 3160, 3120, 2270, 2240, 1720, 1650, 1620, 1595, 1555, 1545, 1685, 1355, 1280, 1145, 1110, and 1065. NMR absorptions ($CDCl_3$, $\delta$) are observed at 7.70, 6.95, 4.25, 4.00, and 3.95.

EXAMPLE 2

5,9-Dimethoxy-2-(1-pyrrolidinyl)-4H-furo[3,2-g][1,3]benzoxazin-4-one (Formula XXIII: $R_3$ and $R_4$ are both methoxy and $R_8$ and $R_9$ are taken together as $-(CH_2)_4-$)

Refer to Chart A.

The title product of Example 1 (4.66 g) is added to acetonitrile (50 ml). To the resulting solution is added pyrrolidine (1.19 g) in a single portion. After 5 min of exothermic reaction, a solid separates from the solution and stirring is continued for 16 hr. Collection of the solid by filtration yields 2.54 g of pure title product. Concentration of the filtrate under reduced pressure, followed by washing, yields an additional 920 mg of pure formula XXIII product. Melting point is 211°-212° C. Silica gel TLC $R_f$ is 0.2 in 5% methanol in trichloromethane. IR absorptions ($cm^{-1}$) are observed at 3120, 3100, 1670, 1620, 1590, 1530, 1485, 1425, 1385, 1340, 1320, 1300, 1240, 1075, and 1050. NMR absorptions ($CDCl_3$, $\delta$) are observed at 7.60, 7.0, 4.15, 4.03, 3.7, and 1.99.

EXAMPLE 3

5,9-Dimethoxy-2-(4-morpholinyl)-4H-furo[3,2-g][1,3]benzoxazin-4-one (Formula XXIII: $R_3$ and $R_4$ are both methoxy and $R_8$ and $R_9$ are taken together as $-(CH_2)_2-O-(CH_2)_2-$)

Refer to Chart A.

Following the procedure of Example 2, the title product of Example 1 (5.54 g), acetonitrile (50 ml), and morpholine (1.74 g) yield 5.5 g of title product, melting point 121°-126° C. Silica gel TLC $R_f$ is 0.22 in 5% methanol in trichloromethane. IR absorptions ($cm^{-1}$) are observed at 3140, 3100, 1675, 1620, 1585, 1540, 1490, 4130, 1375, 1345, 1310, 1265, 1115, 1075, 1050, and 905.

NMR absorptions ($CDCl_3$, δ) are observed at 7.62, 7.02, 4.29, 3.07, and 3.82.

EXAMPLE 4

5,9-Dimethoxy-2-(N,N-dimethylamino)—4-H—furo[3,2-g][1,3]benzoxazin-4-one (Formula XXIII: $R_3$ and $R_4$ are both methoxy and $R_8$ and $R_9$ are both methyl Refer to Chart A.

Following the procedure of Example 2, the title product of Example 1 (10 g), acetonitrile (50 ml), and excess N,N-dimethylamine yield from recrystallization in ethyl acetate 5.14 g of pure title product. Melting point is 194°-196° C. Silica gel TLC $R_f$ is 0.22 in 10% methanol in trichloromethane. IR absorptions ($cm^{-1}$) are observed at 3120, 3100, 1670, 1620, 1580, 1480, 1400, 1340, and 1310. NMR absorptions ($CDCl_3$, δ) are observed at 7.60, 6.97, 4.14, 4.03, and 2.22.

EXAMPLE 5

2-[2-(Hydroxymethyl)-1-pyrrolidinyl]-5,9-dimethoxy-4H-furo[3,2-g][1,3]benzoxazin-4-one (Formula XXIII: $R_3$ and $R_4$ are both methoxy and $R_8$ and $R_9$ taken together are $—CH(CH_2OH)—(CH_2)_3—$)

Refer to Chart A.

The product of Example 1 (5.64 g) is taken up in acetonitrile (50 ml) and 2-pyrrolidine-methanol (2 ml) is added. The resulting solution is then warmed sightly and allowed to stir at ambient temperature for 72 hr. The resulting suspension is then filtered and the filter cake is suspened in 200 ml of ethyl acetate, boiled, and thereafter allowed to cool. Filtration of the resulting ethyl acetate suspension yields 4.68 g of pure title product, melting point 177°-178° C. Silica gel TLC $R_f$ is 0.53 in 10% methanol in trichloromethane. IR absorptions ($cm^{-1}$) are observed at 3300, 3100, 1600, 1615, 1560, 1545, 1485, 1365, 1315, 1235, 1065, 1000, and 775. NMR absorptions ($CDCl_3$, δ) are observed at 7.88, 7.13, 4.18, 4.10, 4.03, 3.95-3.5, 3.3, and 2.3-1.8.

EXAMPLE 6

5,9-Dimethoxy-2-(4-methyl-1-piperazinyl)-4H-furo[3,2-g]benzoxazin-4-one (Formula XXIII: $R_3$ and $R_4$ are both methoxy and $R_8$ and $R_9$ taken together are $—(CH_2)_2—N(CH_3)—(CH_2)_2—$)

Refer to Chart A.

Following the procedure of Example 5, the title product of Example 1 (3.57 g), acetonitrile (35 ml), and N-methylpiperazine (1.5 ml) yield a residue which is chromatographed on silica gel (eluting with 5% methanol in trichloromethane) and subjected to high pressure liquid chromatography over silica gel (eluting with 10% methanol in trichloromethane) to yield 2.8 g of pure title product, melting point 149°-151° C. Silica gel TLC $R_f$ is 0.18 in 10% methanol in trichloromethane. IR absorptions ($cm^{-1}$) are observed at 3120, 3080, 2800, 1675, 1670, 1620, 1590, 1535, 1490, 1345, 1320, 1305, 1270, 1215, 1070, and 1055. NMR absorptions ($CDCl_3$, δ) are observed at 7.66, 7.03, 4.20, 4.11, 4.05-3.80, 2.66-2.40, and 2.38.

EXAMPLE 7

5,9-Dimethoxy-2-(tetrahydro-4H-1,4-thiazin-4-yl)-4H-furo[3,2-g][1,3]benzoxazin-4-one (Formula XXIII: $R_3$ and $R_4$ are both methoxy and $R_8$ and $R_9$ taken together are $—(CH_2)_2—S—(CH_2)_2—$)

Refer to Chart A.

The title product of Example 1 (3.55 g), acetonitrile (35 ml), and thiomorpholine (1.3 ml) are combined. After 3 days a solid is collected by filtration and recrystallization from methanol yielding pure title product, melting point 229°-231° C. Silica gel TLC $R_f$ is 0.60 in 10% methanol in trichloromethane. IR absorptions ($cm^{-1}$) are observed at 3120, 1670, 1585, 1545, 1485, 1350, 1325, 1315, 1260, 1250, and 1065. NMR absorptions ($CDCl_3$, δ) are observed at 8.0, 7.2, 4.15, 4.1-4.0, 3.97, and 3.0-2.4.

EXAMPLE 8

2-[[2-(Diethylamino)-ethyl]ethylamino]-5,9-dimethoxy-4H-furo[3,2-g][1,3]benzoxazin-4-one (Formula XXIII: $R_3$ and $R_4$ are both methoxy, $R_8$ is ethyl, and $R_9$ is 2-(diethylamino)-ethyl)

Refer to Chart A.

The title product of Example 1 (3.54 g), acetonitrile (35 ml), and triethylethylenediamine (2.3 ml) are added and the resulting solution stirred for 72 hr. Concentration under reduced pressure yields an oily residue which is chromatographed under high pressure liquid chromatography on 330 g of silica gel, eluting with 5% methanol in trichloromethane. Pure title product, 3.1 g, is obtained as a yellow oil. Silica gel TLC $R_f$ is 0.1-0.2 in 10% methanol in trichloromethane. IR absorptions ($cm^{-1}$) are observed at 3110, 2810, 1680, 1620, 1575, 1490, 1345, 1325, 1295, 1200, and 1070. NMR absorptions ($CDCl_3$, δ) are observed at 7.65, 7.04, 4.20, 4.12, 3.95-3.5, 2.9-2.4, and 1.5-0.9.

EXAMPLE 9

5,9-Dimethoxy-2-(3-thiazolidinyl)-4H-furo[3,2-g][1,3]benzoxazin-4-one (Formula XXIII: $R_3$ and $R_4$ are both methoxy and $R_8$ and $R_9$ taken together are $—CH_2—S—(CH_2)_2—$)

Refer to Chart A.

The title product of Example 1 (3.65 g), acetonitrile (35 ml), and thiazolidine (1.1 ml) are added. A precipitate forms after about 15 min. Stirring is then continued for 3 days. A solid is thereafter collected on a filter and washed with diethyl ether, methanol, methyl acetate. Pure title product, 3.35 g of a white solid, is thereby obtained. Melting point is 219°-221° C. Silica gel TLC $R_f$ is 0.3 in 5% methanol in trichloromethane. IR absorptions ($cm^{-1}$) are observed at 3120, 3060, 1670, 1625, 1605, 1580, 1550, 1480, 1425, 1345, 1285, 1230, 1060, 1055, and 770. NMR absorptions ($CDCl_3$, δ) are observed at 7.84, 7.20, 5.02, 4.89, 4.3-4.1, and 3.5-3.3.

EXAMPLE 10

2-[[(2S)-6,6-Dimethyl-(bicyclo[3.1.1]hept-2-yl)methyl-]amino]-5,9-dimethoxy-4H-furo[3,2-g][1,3]benzoxazin-4-one (Formula XXIII: $R_3$ and $R_4$ are both methoxy, and $R_8$ and $R_9$ taken together are bicyclo[3.3.1.1.]hept-2-yl-methyl)

Refer to Chart A.

The title product of Example 1 (6.53 g), acetonitrile (70 ml), and myrtylamine (4.50 g) are combined. After stirring for 72 hr, the resulting mixture is filtered and the filter cake washed with 20% diethyl ether in hexane. Chromatography on 450 g of silica gel eluting with 2% methanol in trichloromethane yields 1.5 g of pure title product as an oil. Crystallization from 60 ml ethyl acetate in hexane yields 2.5 g of pure title product as a white solid, melting point 193°-195° C. Silica gel TLC $R_f$ is 0.50 in 10% methanol in trichloromethane. IR absorptions ($cm^{-1}$) are observed at 3080, 1680, 1655, 1615, 1545, 1490, 1420, 1385, 1295, 1220, 1130, 1070, 765, and 720. NMR absorptions ($CDCl_3$, δ) are observed at 7.65, 7.0, 4.15, 3.8-3.4, 2.6-1.7, and 1.7-0.95.

EXAMPLE 11

2-(2,6-Dimethyl-4-morpholinyl)-5,9-dimethoxy-4H-furo[3,2-g][1,3]benzoxazin-4-one (Formula XXIII: $R_3$ and $R_4$ are both methoxy, and $R_8$ and $R_9$ taken together are $-CH_2-CH(CH_3)-O-CH(CH_3)-CH_2-$)

Refer to Chart A.

The title product of Example 1 (2.56 g), acetonitrile (25 ml), and 2,6-dimethylmorpholine (1.2 ml) are combined. After stirring at ambient temperature for 144 hrs, a solid is collected on a filter and washed with diethyl ether (50 ml). Drying yields 1.1 g of pure title product as a white solid, melting point 199.5°-200.9° C. Silica gel TLC $R_f$ is 0.30 in 5% methanol in trichloromethane. IR absorptions ($cm^{-1}$) are observed at 3140, 3100, 3060, 1670, 1615, 1565, 1540, 1485, 1350, 1330, 1295, 1270, and 1070. NMR absorptions ($CDCl_3$, δ) are observed at 7.62, 7.03, 4.18, 4.08, 3.9-3.5, 3.0-2.6, and 1.28.

EXAMPLE 12

5,9-Dimethoxy-4H-furo[3,2-g][1,3]benzoxazine-2,4-dione (Formula XXIV: $R_3$ and $R_4$ are both methoxy)

Refer to Chart A.

The product of Example 4 (3.5 g) is taken up in 150 ml of dry methanol and stirred. Anhydrous hydrochloric acid is bubbled into the solution vigorously for 60 seconds and the resulting solution then heated to reflux under a nitrogen atmosphere for 6 hrs. The mixture is then allowed to return to ambient temperature for 36 hrs, and a crystalline percipitate is collected on a filter and washed with diethyl ether (100 ml). As a result, 1.59 g of pure title product is obtained as a white solid, melting point 240°-242° C. Concentration of the filtrate to dryness yields an additional 0.22 g of pure title product. Silica gel TLC $R_f$ is 0.51 in 10% methanol in trichloromethane. IR absorptions ($cm^{-1}$) are observed at 3160, 3140, 3060, 1765, 1705, 1600, 1555, 1485, 1345, 1215, 1145, 1085, 1040, 760, and 745. NMR absorptions ($CDCl_3$, δ) are observed at 7.64, 7.04, 4.16, and 4.18.

EXAMPLE 13

6-Hydroxy-4,7-dimethoxy-5-benzofurancarboxamide (Formula XXXII: $R_3$ and $R_4$ are both methoxy)

Refer to Chart B.

6-Hydroxy-4,7-dimethoxy-5-benzofurancarboxylic acid methyl ester (4.0 g) is added to a saturated aqueous solution of methanol (100 ml). The resulting mixture is then heated at reflux for 2.5 hrs to obtain a cream colored solid precipitate. Cooling in an ice bath and filtration yields 3.1 g of pure title product, melting point 186°-187° C. Silica gel TLC $R_f$ is 0.6 in 10% methanol in trichloromethane. IR absorptions ($cm^{-1}$) are observed at 3440, 3320, 3240, 3200, 2700, 2660, 2580, 2340, 1650, 1610, 1580, 1550, 1440, 1420, 1410, 1285, 1150, and 1075. NMR absorptions ($CDCl_3$, δ) are observed at 7.9, 7.18, 4.15, and 3.89.

EXAMPLE 14

2',3',5',6'-Tetrahydro-5,9-dimethoxy-spiro[2H-furo[3,2-g][1,3]benzoxazine-2,4'-[4H]thiopyran]-4(3H)-one (Formula XXXIV: $R_3$ and $R_4$ are both methoxy, and $R_1$ and $R_2$ are taken together as $-(CH_2)_2-S-(CH_2)_2-$)

Refer to Chart B.

A solution of the product of Example 13 (4 g) in toluene (50 ml) is treated under a nitrogen atmosphere with tetrahydrothiopyran-4-one (3.4 g) and pyrrolidine (1.0 ml). After heating to reflux for 17 hrs, the resulting solution is then allowed to cool to ambient temperature, diluted with ethyl acetate (50 ml) and washed with 2 N aqueous hydrochloric acid and brine. The organic phase is then dried over sodium sulphate and concentrated under reduced pressure to yield a tan solid, which when washed thoroughly with diethyl ether yields 4.3 g of pure title product as a white solid, melting point 154°-155° C. An analytically pure sample is obtained by high pressure liquid chromatography on 330 g of silica gel eluting with 10% ethyl acetate in trichloromethane. Melting point is 163°-165° C. Silica gel TLC $R_f$ is 0.32 in ethyl acetate. IR absorptions ($cm^{-1}$) are observed at 3160, 3060, 3120, 1670, 1620, 1605, 1545, 1495, 1485, 1365, and 1075. NMR absorptions ($CDCl_3$, δ) are observed at 7.60, 6.69 4.11, and 3.1-2.1.

EXAMPLE 15

5',9'-Dimethoxy-spiro[cyclohexane-1,2'-[2H]furo[3,2-g][1,3]benzoxazin-4'(3'H)-one (Formula XXXIV: $R_3$ and $R_4$ are both methoxy, and $R_1$ and $R_2$ taken together are $-(CH_2)_5-$)

Refer to Chart B.

Following the procedure of Example 14, the title product of Example 13 (0.90 g) cyclohexanone (3 ml) and pyrrolidine (0.8 ml) are transformed to 1.12 g of pure Formula XXXIV title product, melting point 169°-171° C. Silica gel TLC $R_f$ is 0.3 in 25% ethyl acetate in hexane. IR absorptions ($cm^{-1}$) are observed at 3180, 3060, 1670, 1620, 1560, 1540, 1485, 1440, 1370, 1075, and 980. NMR absorptions ($CDCl_3$, δ) are observed at 7.50, 6.95, 4.08, 4.05, and 2.2-1.2.

EXAMPLE 16

2,2-Diethyl-2,3-dihydro-5,9-dimethoxy-4H-furo[3,2-g][1,3]benzoxazin-4-one (Formula XXXIV: $R_3$ and $R_4$ are both methoxy, and $R_1$ and $R_2$ are both ethyl)

Refer to Chart B.

Following the procedure of Example 14, the title product of Example 13 (1.53 g) 3-pentanone, and pyrrolidine (0.5 ml) yields 1.0 g of pure title product as a white solid, melting point 148.5°-151.8° C. Silica gel TLC $R_f$ is 0.29 in ethyl acetate. IR absorptions ($cm^{-1}$) are observed at 3160, 3120, 3060, 1665, 1615, 1540, 1490, 1380, 1350, 1240, 1130, 1080, and 1065. NMR absorptions ($CDCl_3$, δ) are observed at 7.51, 6.90, 6.5, 4.08, 1.87, and 1.00.

EXAMPLE 17

2,3-Dihydro-5,9-dimethoxy-2-methyl-2-[(methylthio)-methyl]-4H-furo[3,2-g][1,3]benzoxazin-4-one (Formula XXXIV:

Refer to Chart B.

Following the procedure of Example 14, the product of Example 13 (3.9 g), thiomethyl acetone (5.5 ml) and pyrrolidine (1 ml) yields 1.24 g of pure title product, melting point 121.5°-122.6° C. Silica gel TLC $R_f$ is 0.26 in 50% ethyl acetate in hexane. IR absorptions ($cm^{-1}$) are observed at 3180, 3120, 3060, 1767, 1625, 1545, 1490, 1385, 1370, 1125, 1080, and 1070. NMR absorptions ($CDCl_3$, δ) are observed at 8.38, 7.56, 6.93, 4.10, 4.05, 3.04, 2.18, and 1.80.

EXAMPLE 18

5,9-Dimethoxy-2,2-dimethyl-2,3-dihydro-4H-furo[3,2-g][1,3]benzoxazine-4-one (Formula XXXIV: $R_3$ and $R_4$ are both methoxy, and $R_1$ and $R_2$ are both methyl Refer to Chart B.

Following the procedure of Examples 14-17 above, the product of Example 13 is transformed to the title product. IR absorptions ($cm^{-1}$) are observed at 3160, 3060, 3120, 1680, 1620, 1540, 1485, 1370, 1245, 1125, 1075, and 1065. NMR absorptions ($CDCl_3$, δ) are observed at 7.63, 6.95, 4.15, 4.05, and 1.72.

EXAMPLE 19

4,9-Dimethoxyfuro[3,2-g]phthalazin-5(6H)-one (Formula XLIII: $R_3$ and $R_4$ are both methoxy)

Refer to Chart C.

6-Formyl-4,7-dimethoxy-5-benzofurancarboxylic acid methyl ester (1.05 g) is added to absolute ethanol (20 ml). To the resulting solution is added hydrazine (1.5 ml). After heating the resulting mixture to reflux for 16 hrs, the reaction is cooled to 0° C. and the resulting solid which separates from the reaction mixture is collected by filteration to yield 480 mg of title product. The filtrate is then evaporated under reduced pressure and the resulting solid collected by filteration to yield an additional 220 mg of product. Recrystallization from acetonitrile yields analytically pure title product, melting point 239.5°-241° C. Silica gel TLC $R_f$ is 0.26 in 5% methanol in trichloromethane. IR absorptions ($cm^{-1}$) are observed at 3160, 3020, 3120, 1655, 1610, 1600, 1570, 1550, 1540, 1485, 1350, 1230, and 1080. NMR absorptions ($CDCl_3$, δ) are observed at 8.4, 8.3., 7.35, 4.25, and 3.95.

Accordingly, following the procedure of the examples above, there are obtained each of the various compounds of formulas I, II, or III.

FORMULAS

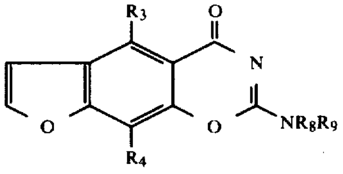

I

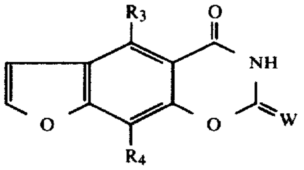

II

-continued

FORMULAS

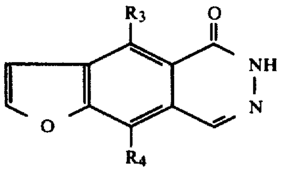

III

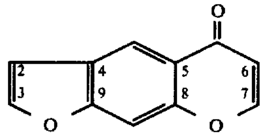

IV

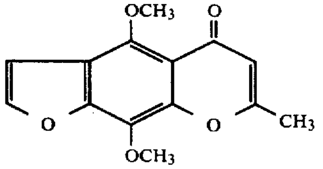

V

CHART A

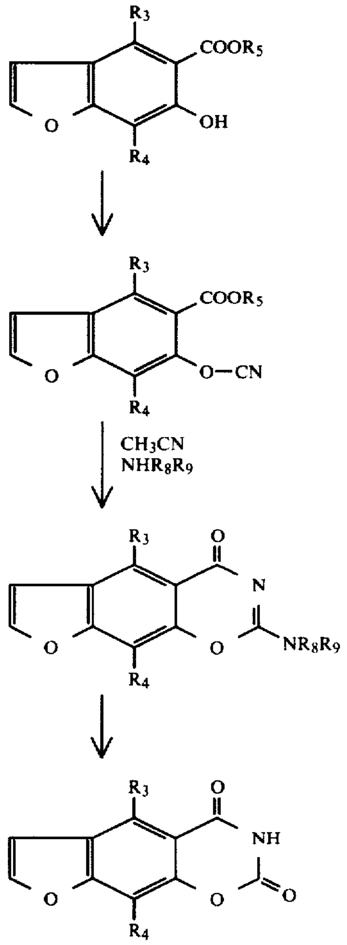

XXI

XXII

XXIII

XXIV

CHART B

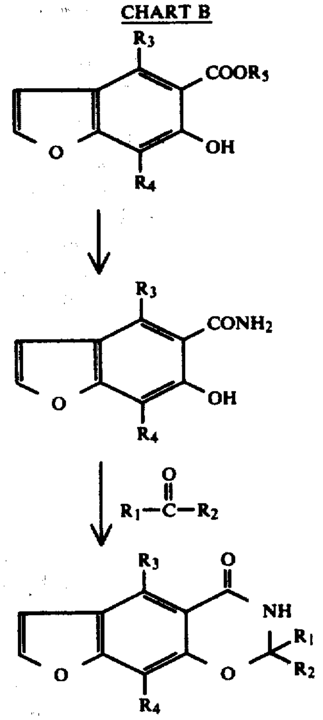

XXXI

XXXII

XXXIII

XXXIV

CHART C

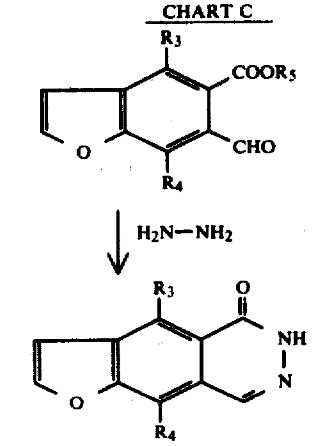

XLI

XLII

XLIII

APPENDIX A

Composition and Process

BACKGROUND OF THE INVENTION

THe present invention provides novel compositions of matter and processes for their preparation. Particularly, the present invention relates to novel chemical intermediates and associated processes for the preparation of furochromones. Most especially, the present invention provides for the preparation of novel antiatherosclerotic furochromones, particularly khellin analogs.

Khellin and related compounds are known to exert a wide variety of pharmacological effects. Recently, khellin has been reported to exhibit useful antiatherosclerotic activities. Moreover, numerous analogs of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73:2960 (1951), Murti, V. V. S., et al., Proc. of the Indian Acad. of Sci., 30A:107 (1949), and Geissman, T. A., et al., J. Am. Chem. Soc., 73:1280 (1951). Also descriptive of the synthesis of khellin are Spath, E., et al., Chem. Ber., 71:106 (1938), Dann, O., et al., Chem. Ber., 93:2829 (1960), Dann, O., et al., Ann. Chem., 605:146 (1957), and Murti, V. V. S., et al., J. Sci. Ind. Res. (India), 8B:112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93:297 (1960), Aneja, R., et al., J. Sci. Ind. Res. (India), 17B:382 (1958), Gardner, T. S., et al., J. Org. Chem., 15:841 (1950), and Rowe, L. R., et al., Indian J. Chem., 5:105 (1967).

Accordingly, the references cited above described the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital.,

PRIOR ART

Methods of the total synthesis of khellin are known, as are certain chemical intermediates useful in its synthesis.

Most typically, however, the total synthesis of furochromones from benzofurans has been accomplished by utilizing a substituted benzene ring from which to synthesize the fused benzofuran ring system. C. Mustafa, "Benzofurans," John Wiley and Sons, 1974, and Mustafa, A., "Furopyrans and Furopyrones, Chapter 3: Furochromones," John Wiley and Sons, New York, N.Y., 1967.

U.S. Pat. No. 4,284,569 provides a variety of novel antiatherosclerotic furochromones.

SUMMARY OF THE INVENTION

The present invention particularly provides:

(a) A process for preparing a compound of formula XI which comprises:

(1) reacting the lithium dianion of a compound of formula X with succinic anhydride;

(2) $C_1$-$C_4$ alkyl esterfying the resulting formula XII ketodiacid of step (1);

(3) reacting the resulting formula XIII ketodiester of step (2), wherein $R_{11}$ is $C_1$-$C_4$ alkyl, with an amide acetal of formula XIV, wherein $R_3$ and $R_4$, being the same or different, are $C_1$-$C_4$ alkyl;

(4) cyclizing of the resulting formula XV compound of step (3), wherein $R_3$, $R_4$ and $R_{11}$, are as defined above;

(5) dialkylating the resulting formula XVI benzofuran of step (4), wherein $R_{11}$ is as defined above;

(6) oxidizing the resulting formula XVII dialkoxybenzofuran of step (5), wherein $R_1$ is $C_1$-$C_4$ alkyl and $R_{11}$ is as defined above; and (7) reducing the resulting formula XVIII compound of step (6), wherein $R_2$ and $R_{11}$ are as defined above, to the formula XI compound;

(b) A furochromone intermediate of formula I or II, wherein $R_{11}$ is $C_1$–$C_4$ alkyl; wherein $R_2$ is hydrogen or $C_1$–$C_4$ alkyl; and wherein $R_{11}$ is as defined above; wherein W is α-H:β-H or =CH—$NR_3R_4$; wherein $R_3$ and $R_4$, being the same or different, are as defined above;

(c) A furochromone intermediate of formula III;

(d) A furochromone intermediate of formula IV, wherein $R_{11}$ is as defined above;

(e) A furochromone intermediate of formula V, wherein $R_3$, $R_4$ and $R_{11}$ are as defined as above;

(f) A furochromone intermediate of formula VI, wherein $R_{11}$ is as defined above;

(g) A furochromone intermediate of formula VII, wherein $R_{11}$ is as defined above;

(h) A furochromone intermediate of formula I or II, wherein $R_1$, $R_3$, $R_4$, and $R_{11}$ are all methyl; and (i) An anti-atherosclerotic furochromone of formula VIII wherein $R_{10}$ is $C_2$–$C_4$ alkyl;

wherein $R_{12}$ is:

(1) hydrogen;

(2) $C_1$–$C_8$ alkyl;

(3) $C_2$–$C_8$ alkoxymethyl;

(4) $C_2$–$C_8$ alkylthioalkyl;

(5) trifluoromethyl;

(6) phenoxymethyl optionally substituted by chloro, fluoro, trifluoromethyl, $C_1$–$C_3$ alkyl or $C_1$–$C_3$ alkoxy;

(7) phenylthiomethyl optionally substituted by chloro, fluoro, trifluoromethyl, $C_1$–$C_3$ alkyl or $C_1$–$C_3$ alkoxy;

(8) —$CH_{21}$—$S(O)_n$-$R_{20}$, wherein n is zero, one, or 2 and $R_{20}$ is $C_1$–$C_5$ alkyl; or (9) —$CH_2NR_8R_9$, wherein $R_8$ and $R_9$ are hydrogen, $C_1$–$C_{12}$ alkyl or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by $C_1$–$C_4$ alkyl, $C_2$–$C_8$ alkylthiomethyl or alkoxymethyl $C_1$–$C_4$ hydroxyalkyl, or phenyl;

wherein $R_{13}$ is:

(1) hydrogen;

(2) chloro, iodo, or bromo; or (3) —$CH_2$—$S(O)_n$—$R_{20}$ wherein n and $R_{20}$ are as defined above, with the proviso that $R_{13}$ is —$CH_2$—$S(O)_n$—$R_{20}$ only when $R_{14}$ is methyl.

In accordance with the method described above, there is prepared the formula XI benzofuran when $R_1$ is methoxy. This formula XI benzofuran is known to be useful in the preparation of a wide variety of antiatherosclerotic substances, including khellin and various analogs thereof. See U.S. Pat. No. 4,284,569. Similarly there are prepared the novel formula XI benzofurans when $R_1$ is $C_2$–$C_4$ alkoxy. These intermediates are useful in the preparation of novel antiatherosclerotic 4,9-di-($C_2$–$C_4$)-alkoxy-furochromones of formula VIII by means described in U.S. Pat. No. 4,284,569 for the preparation of the corresponding 4,9-dimethoxyfurochromones therein. Moreover, the manner of use of the novel 4,9-di-($C_2$–$C_4$)-alkoxy-furochromones of formula VIII in the treatment and prevention of atherosclerosis is the same as that described in U.S. Pat. No. 4,284,569 for the corresponding 4,9-dimethoxy compounds. Accordingly, the manner of the preparation and pharmacological use of these novel formula VIII compounds is incorporated herein by and reference from the description of the preparation and use in U.S. Pat. No. 4,284,569 of the anti-atherosclerotic 4,9-dimethoxyfurochromones. Among the novel formula VIII compounds herein, the 4,9-diethoxyfurochromones are preferred.

The process of the present invention is more completely understood by reference to the charts below. In these charts, $R_1$, $R_3$, $R_4$, $R_{11}$ $R_{12}$, and $R_{13}$ are as defined above. $R_5$ is:

(a) hydrogen;

(b) $C_1$–$C_8$ alkyl;

(c) $C_2$–$C_8$ alkoxymethyl;

(d) $C_2$–$C_8$ alkylthioalkyl;

(e) trifluromethyl;

(f) phenoxymethyl;

(g) phenylthiomethyl;

(h) phenoxymethyl or phenylthiomethyl, either of which is optionally substituted by one chloro, fluoro, trifluoromethyl, $C_1$–$C_3$-alkyl, or $C_1$–$C_3$-alkoxy; or (i) $C_3$–$C_{10}$ cycloalkyl.

With regard to the substituent W in formula I, this moiety is defined as either =CH—$NR_3R_4$ or α-H:β-H. In the latter case reflects the fact that each of the valances of the moiety W is a hydrogen atom, one of which is attached in the α configuration with respect to the ring and the other which is attached in the β configuration with respect to the ring.

The carbon atom content of various hydrocarbon containing moieties is indicated by a prefix designating the minimum and maximum number of carbon atoms in the moiety, i.e., the prefix $C_i$–$C_j$ indicates a carbon atom content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the charts, Chart A provides a method whereby the known formula XXI compound, 3-furoic acid is transformed to the highly functionalized benzofuran intermediate of formula XXVI useful in the synthesis of khellin and khellin analogs.

With further respect ot chart A, the formula XXII compound is prepared from the formula XXI compound by first preparing the dianion of the formula XXII compound. See Knight, D. W., et al., J. Chem. Soc. Perkins, 1125 (1981), and references cited therein. Accordingly, this dianion is generated by treatment of the formula XXII compound with two equivalents of lithium diisopropylamide at low temperature, e.g., −78° C. At this temperature the resulting dianion is stable for several hours.

The dianion is then transformed to the formula XXII compound by treatment with succinic anhydride.

The resulting formula XXII is then esterified to the formula XXIII compound by conventional means. For example, an etherial diazoalkane is employed or, for larger scale synthesis, an alkanol in hydrochloric acid is useful.

The formula XXIII compound is then converted to the formula XXIV compound by reaction at elevated temperature with an N,N-dialkylformamide dimethylacetal. Preferably, N,N-dimethylformamide dimethylacetal is employed at temperatures in excess of 80° C. For example, reaction at 100° C. for 2 hr yields the formula XXIV compound.

Although this reaction preceeds in relatively high yield at elevated temperature, a less complex mixture of products is obtained by reacting the formula XXIII with the desired formamide for prolonged periods. i.e., up to a week. The optimal conditions for the preparation of the formula XXIV compound by this method are the stirring of the formula XXIII reactant in neat N,N-dimethylformamide dimethylacetal employing a trace of p-toluenesolfonic acid. Alternatively base catalysis is employed using alkoxides, e.g., potassium tertbutoxide in an organic solvent.

The formula XXV compound is then prepared from the formula XXIV compound by a Dieckmann cyclization. Preferably the cyclization occurs under basic conditions, e.g., preferably using potassium tertbutoxide in organic solvent, followed by an acid quench. Suitable organic solvents include benzene and tert-butanol, although the preferred solvent is tetrahydrofuran.

Finally, the formula XXVI compound of Chart A is prepared from the formula XXV compound by alkylation. Alkylation can be accomplished quantitatively by treatment of the formula XXV reactant with an alkyliodide in potassium carbonate.

Chart B provides a method whereby the formula XXXI compound, prepared as the formula XXVI compound of Chart A is converted to formula XXXIII intermediate, a compound known to be useful in the preparation of both khellin and analogs thereof. In accordance with the procedure of Chart B, the formula XXXI compound is transformed to the formula XXXII compound by a Baeyer Villager oxidation. For this oxidation, m-chloroperbenzoic acid is employed at ambient temperature in an organic solvent. Tetrahydrofuran or isopropanol represents the preferred solvent for undertaking this oxidation.

Finally, the formula XXXII compound is transformed into the formula XXXIII compound by conversion of the ester group to a methyl ketone. For this purpose a Grignard reagent in the presence of a tertiary amine is employed according to the method of Kikkawa, I., and Yorifuji, T., Synthesis, 887 (1981).

Chart C provides a summary of the method by which the formula XLI compound, prepared as the formula XXXIII compound of Chart B, is transformed to khellin or analogs thereof. The procedures of Chart C are, for example, known in the art from U.S. Pat. No. 4,284,569, wherein Charts A-D of that patent describe the synthesis of the various formula XLII and formula XLIII compounds from the formula XLI starting material.

Accordingly, the charts herein provide a description of the preparation and use of the novel process and compounds of the present invention.

DESCRIPTION OF THE PREFERRED EMBODIMENTS

The present disclosure is more fully understood by the operation of the following examples:

EXAMPLE 1

3-Carboxy-γ-oxo-2-furanbutanoic acid (Formula XXII).

Refer to Chart A.

Diisopropylamine (202 g) is added to a flame dried 3 neck flask with a mechanical stirrer, droping funnel and nitrogen inlet. To this amine is added tetrahydrofuran (THF, 600 ml). This solution is then cooled to −78° C. and n-butyllithium (128 g in hexane, 1.6 m) added over 20 min. After completion addition of the n-butyllithium the reaction is stirred for 2.5 h, the last hour of which, the reaction vessel was only 25% submerged in the dry ice bath. At this point, the lithium diisopropylamine (LDH) separates from solution. Two liters of THF are added and a homogeneous solution developes. The reaction is then completely submerged in the dry ice bath and the 3-furoic acid, formula XXI (100 g), in THF (600 ml) is added over 30 minutes. After complete addition of 3-furoic acid the reaction is stirred an additional two hours. At this point, succinic anhydride (100 g) in THF (800 ml) is rapidly added via the addition funnel. A solid almost immediately begins to separate from solution. As the reaction warms to room temperature, quenching is effected with 2 N hydrochloric acid (3 liters). The entire reaction is poured into a portable separatory funnel. The organic layer is separated and the aqueous back extracted with trichloromethane (3 liters). The organic extracts are dried ($MgSO_4$) and solvent removed in vacuo to give an off-white solid which after an ether wash afforded 120 g of pure white title, mp 181°-200° C. IR absorption ($cm^{-1}$) absorptions are observed at 3140, 3120, 2740, 2640, 1740, 1705, 1630, 1615, 1570, 1330, 1270, 1215, 1165, 890 and 775. $^1H$-NMR absorptions (δ, $CDCl_3$) are observed at 7.73, 7.05, 3.38 and 2.71. Mass spectral peaks are observed at 212, 194, 176, 167, 150, 149, 140, 139, 95, 55 and 39.

EXAMPLE 2

3-Carboxy-γ-oxo-2-furanbutanoic acid bis (methyl ester) (Formula XXIII: $R_{11}$ is methyl).

Refer to Chart A.

The formula XXII product of Example 1 (170 mg) is suspended in trichloromethane (10 ml) and treated with excess diazomethane. When TLC (5% EtOAc/$CHCl_3$) indicated complete conversion to the bismethyl ester, the trichloromethane is removed in vacuo to yield 211 mg of crude product which was chromatographed (Merck B, 5% EtOAc/$CHCl_3$) to yield 211 mg of the pure title product as a colorless oil.

Silica Gel TLC $R_f$ is 0.39 in 5% ethyl acetate in trichloromethane. IR absorptions ($cm^{-1}$) are observed at 3050, 1735, 1695, 1590, 1480, 1440, 1400, 1360, 1305, 1280 and 1160. $^1H$-NMR absorptions (δ, $CDCl_3$) are observed at 7.5, 6.83, 3.90, 3.71, 3.30, and 2.75. Mass spectral peaks are observed at 240, 208, 181, 176, 153, 149, 123, 95, 55 and 38.

EXAMPLE 3

β-[(Dimethylamino)methylene]-3-(methoxycarbonyl)-γ-oxo-2-furanbutanoic acid bis (methyl ester) (Formula XXIV: $R_3$, $R_4$ and $R_{11}$ are all methyl).

Refer to Chart A.

The formula XXIII product of Example 2 (500 mg) and N,N-dimethylformamide dimethylacetal (230 mg) are heated neat at 100° C. for 1 hour. The reaction is then cooled to room temperature and excess acetal and methanol are removed in vacuo. The resulting brown oil is chromatographed (eluting with 5% methanol in ethyl acetate) to yield 280 mg of title product as a yellow oil.

Silica Gel TLC $R_f$ is 0.4 in 5% methanol in ethyl acetate. IR absorptions ($cm^{-1}$) are observed at 3120, 2950, 1725, 1640, 1560, 1430, 1405, 1390, 1320 and 1160.

NMR absorptions (δ, $CDCl_3$) are observed at 7.45, 6.95, 6.73, 3.82, 3.68 and 3.07. Mass spectral peaks are observed at 295, 263, 264, 237, 236, 218, 182, 153, 142 and 139.

EXAMPLE 4

6-Formyl-4,7-dihydroxy-5-benzofurancarboxylic acid methyl ester (Formula XXV: $R_{11}$ is methyl).

Refer to Chart A.

A. (Preparation 1) Potassium metal (50 mg, 1.28 mmol) is added to tert-butanol (5 ml) under nitrogen with stirring. After the potassium metal has dissolved the formula (190 mg), in tert-butanol (5 ml) is added at room temperature. As the drops of diester hit the solution, a deep red color developes. This color slowly fades to yellow with time. After complete addition of the formula XXIV product of Example 3, the reaction is stirred an additional hour and then diluted with water. The reaction acidified with 2 N HCl and was extracted with diethyl ether and then with trichloromethane. The combined organic extracts are dried ($MgSO_4$) and solvent removed in vacuo to yield a brown solid which after chromatography affords 40 mg of title product.

Silica Gel TLC $R_f$ is 0.50 in 5% EtOAc/$CHCl_3$. IR absorptions ($cm^{-1}$) are observed at 3500, 2600, 1670, 1640, 1580, 1430, 1360, 1300, 1250. NMR absorptions (δ, $CDCl_3$) are observed at 10.5, 7.81, 7.0 and 4.0. Mass spectral peaks are observed at 236, 205, 204, 203, 176, 149, 148, 147, 119 and 63.

B. (Preparation 2) Potassium tert-butoxide (319 mg) is added to 20 ml of dry THF under nitrogen. This mixture is then cooled to −78° C. and the formula XXIV starting material (420 mg) in THF (15 ml) added via syringe pump at a rate of 0.23 ml/min. A deep red color developes. After complete addition the reaction is stirred an additional 30 minutes and then the reaction is quenched at −78° C. by the addition of 2 N HCl. The reaction is then warmed to room temperature and poured into a separatory funnel. Then 2 N HCl (50 ml) is added and the reaction was extracted with ethyl acetate (3×75 ml). The aqueous layer is then extracted with trichloromethane. The combined organic extracts are dried ($MgSO_4$) and solvent removed in vacuo to 340 mg of a brown solid. This solid is chromatographed over silica gel eluting with 5% ethyl acetate in trichloromethane to yield 200 mg of title product.

EXAMPLE 5

6-Formyl-4,7-dimethoxy-5-benzofurancarboxylic acid methyl ester (Formula XXVI: $R_1$ and $R_{11}$ are methyl).

Refer to Chart A.

6-Formyl-4,7-dihydroxy-5-benzofurancarboxylic acid methyl ester (Example 4, 4.70 g) is added to acetone (100 ml) followed by addition of methyliodide (5.65 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried ($MgSO_4$) and solvent removed in vacuo to yield a yellow oil. Chromatography over 100 g of silica gel eluting with 5% ethyl acetate in trichloromethane affords 5.2 g of title product as a pale yellow oil that slowly crystallized on standing. A pure product is prepared by recrystallization from methanol, mp 89.9°-90.8° C.

Silica Gel TLC $R_f$ is 0.44 in 5% EtOAc/$CHCl_3$. IR absorptions ($cm^{-1}$) are observed at 1730, 1680, 1600, 1470, 1440, 1390, 1340, 1305, 1290, 1060, 980 and 930. NMR absorptions (δ, $CDCl_3$) are observed at 10.4, 7.83, 6.97, 4.38 and 3.98. Mass spectral peaks are observed at 264, 249, 236, 233, 221, 205, 203, 189 and 147.

EXAMPLE 6

6-Hydroxy-4,7-dimethoxy-5-benzofurancarboxylic acid, methyl ester (Formula XXXLII: $R_1$ and $R_{11}$ are methyl).

Refer to Chart B.

A. (Procedure I) A solution of 6-Formyl-4,7-dimethoxy-5-benzofurancarboxylic acid, methyl ester (Example 5, 104.0 mg) in isopropanol (8.0 ml) is treated with 85% m-chloroperbenzoic acid (MCPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried ($MgSO_4$). The residue is chromatographed (20 g silica gel) eluting with 20% ethyl acetate in isomeric hexanes (Skellysolve B) to provide 63.2 mg of white solid, title product, mp 82°-4° (yield 63%).

B. Procedure II) When the reaction is repeated as above substituting THF as the solvent, 101.5 mg of starting material and 184 mg of MCPBA yields 30.0 mg of pure product, mp 82°-84°.

EXAMPLE 7

1-(6-Hydroxy-4,7-dimethoxy-5-benzofuranyl)-ethanone (Formula XXXIII; $R_1$ is methyl).

A. A 100 ml 3 neck flask is oven dried and cooled under nitrogen. Benzene (10 ml) is placed in the flask followed by methyl magnesium bromide (2.9 M in diethyl ether, 2.0 ml). To that solution is added dry triethylamine (2.45 ml) and the resulting mixture is cooled to 8°-10°. A solution of 6-hydroxy-4,7-dimethoxy-5-benzofurancarboxylic acid methyl ester (Example 6, 250 g) in dry benzene (15 ml) is then added dropwise to the cold reaction mixture over a 15 min period. The resulting mixture is yellow; the ice bath is removed and stirring continued at ambient temperature for 6.5 hours.

B. The reaction mixture is then cooled in ice and quenched by the addition of saturated ammonium chloride (10 ml). Diethyl ether (40 ml) is next added, along with 2 N HCl (30 ml). The layers are separated, the ether layer dried ($MgSO_4$) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried ($MgSO_4$). Evaporation of the solvent yields 0.13 g of yellow solid which is chromatographed (on silica gel eluting with 20% ethyl acetate in Skellysolve B SSB eluent) to afford 0.128 g of title product. Recrystallization of that material (hexane/ethyl acetate, 10:1) yields 85 mg of pure, bright yellow title product as a solid.

The product of Example 7 is identical to the product of Example 1 of U.S. Pat. No. 4,284,569 and is accordingly useful for the preparation of khellin and analogs thereof, e.g., see Examples 2-21 of U.S. Pat. No. 4,284,569.

EXAMPLE 8

7-methylthiomethyl-4,9-diethoxyfurochromone (Formula XLIII: $R_1$ is ethyl, $R_{12}$ is methylthiomethyl, and $R_{13}$ is methyl).

Refer to Chart C.

A. 6-Formyl-4,7-dihydroxy-5-benzofurancarboxylic acid methyl ester (Example 4, 4.70 g) is added to acetone (100 ml) followed by addition of ethyliodide (5.80 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried ($MgSO_4$) and solvent removed in vacuo to yield a residue. Chromatography over 100 g of silica gel eluting with 5% ethyl acetate in trichloromethane affords product.

B. A solution of 6-Formyl-4,7-diethoxy-5-benzofurancarboxylic acid, methyl ester (part A, 105.0 mg) in isopropanol (8.0 ml) is treated with 85% m-chloroperbenzoic acid (m-CPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried ($MgSO_4$). The residue is chromatographed (20 g silica gel) eluting with 20% ethyl acetate in isomeric hexanes (Skellysolve B) to provide product.

C. A 100 ml 3 neck flask is oven dried and cooled under nitrogen. Benzene (10 ml) is placed in the flask followed by methyl magnesium bromide (2.9 M diethyl ether, 2.0 ml). To that solution is added dry triethylamine (2.45 ml) and the resulting mixture is cooled to 8°-10°. A solution of 6-hydroxy-4,7-dimethoxy-5-benzofurancarboxylic acid methyl ester (part B, 250 g) in dry benzene (15 ml) is then added dropwise to the cold reaction mixture over a 15 min period. The ice bath is removed and stirring continued at ambient temperature for 6.5 hours.

D. The reaction mixture of part C is then cooled in ice and quenched by the addition of saturated ammonium chloride (10 ml). Diethyl ether (40 ml) is next added, along with 2 N HCl (30 ml). The layers are separated, the ether layer dried ($MgSO_4$) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried ($MgSO_4$). Evaporation of the solvent yields a residue which is chromatographed (on silica gel eluting with 20% ethyl acetate in Skellysolve B eluent) to afford product.

E. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of part D (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

FORMULAS

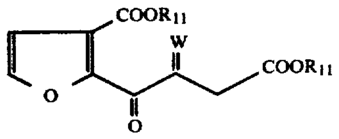
I

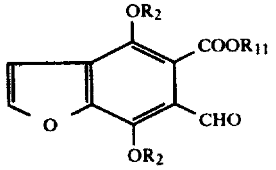
II

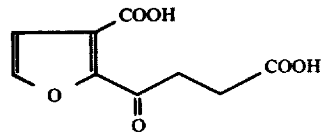
III

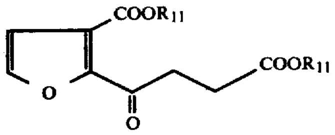
IV

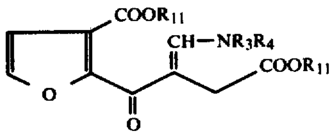
V

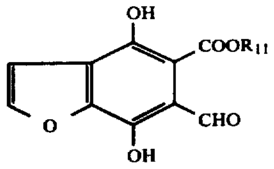
VI

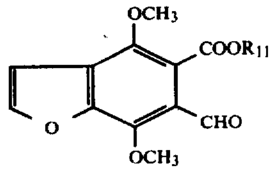
VII

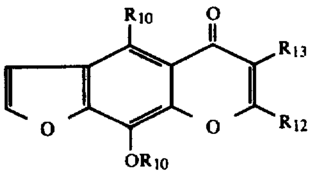
VIII

-continued
FORMULAS
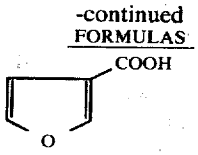
X
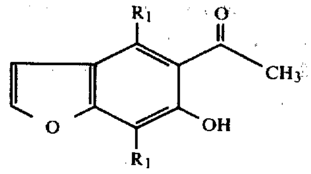
XI
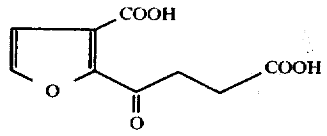
XII
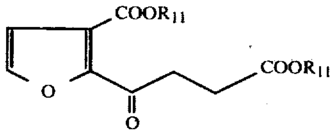
XIII
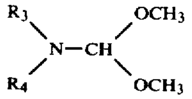
XIV
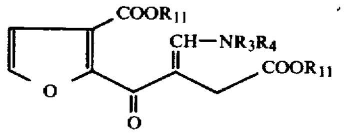
XV
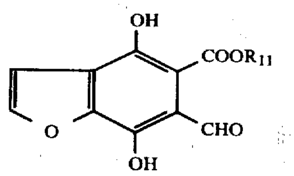
XVI
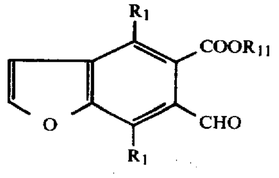
XVII
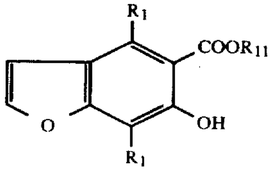
XVIII
CHART A
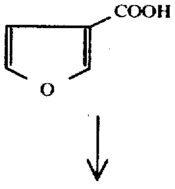
XXI
-continued
CHART A
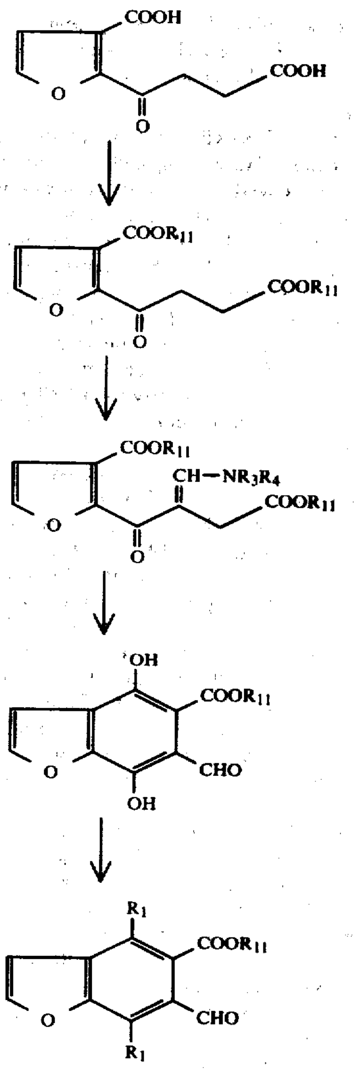
XXII
XXIII
XXIV
XXV
XXVI
CHART B
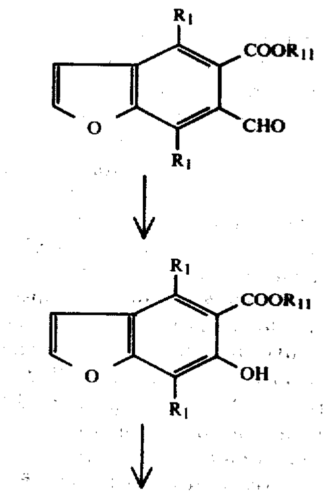
XXXI
XXXII -continued

CHART B

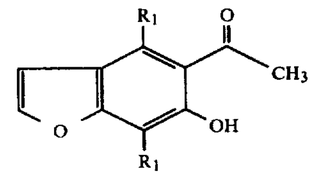

XXXIII

CHART C

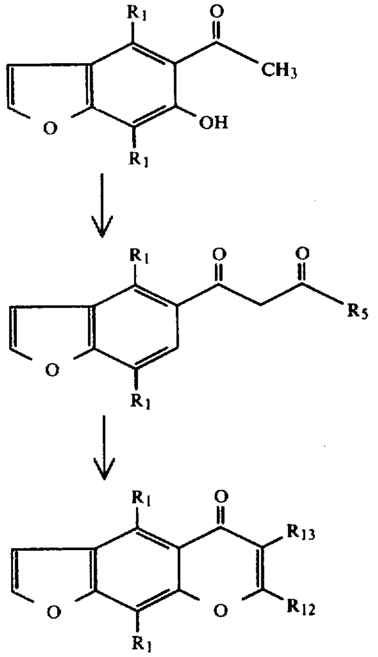

XLI

XLII

XLIII

I claim:

1. An antiatherosclerotic compound of formula I, II, or III

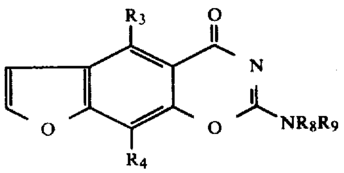

I

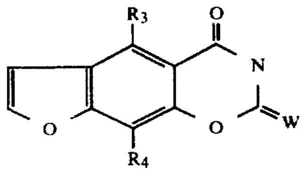

II or

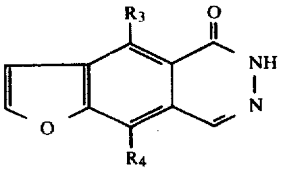

III wherein W is oxo (=O) or α-$R_1$:β-$R_2$, wherein $R_1$ and $R_2$, being the same or different, are individually:

(a) $C_1$–$C_6$ alkyl,
(b) trifluoromethyl,
(c) $C_5$–$C_{10}$ cycloalkyl with the proviso that the cycloalkyl ring is $C_5$–$C_7$,
(d) $C_2$–$C_8$ alkoxyaminoalkyl,
(e) $C_2$–$C_8$ alkoxyalkyl,
(f) $C_2$–$C_8$ alkylthioalkyl,
(g) $C_2$–$C_8$ alkylsulfinylalkyl,
(h) $C_2$–$C_8$ alkylsulfonylalkyl,
(i) $C_7$–$C_{12}$ phenoxyalkyl optionally substituted on the phenyl ring by one, 2, or 3,
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl,
(j) $C_7$–$C_{12}$ phenylthioalkyl optionally substituted on the phenyl ring by one, 2, or 3,
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl,
(k) phenyl optionally substituted by one, 2, or 3,
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl,
(l) aralkyl optionally substituted on the aromatic ring by one, 2, or 3,
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl,
(m) 2- or 3-furanyl optionally substituted by
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl,
(n) 2- or 3-thenyl optionally substituted by
  (i) hydroxy,
  (ii) $C_1$–$C_3$ alkoxy,
  (iii) $C_1$–$C_3$ alkyl,
  (iv) trifluoromethyl,
  (v) halo which is fluoro, chloro, or bromo, with the proviso that not more than two such substituents are other than alkyl, or
(o) $-(CH_2)_pNR_{10}R_{11}$ wherein p is one, 2, or 3, and $R_{10}$ and $R_{11}$, being the same or different, are individually,
  (i) hydrogen,
  (ii) $C_1$–$C_8$ alkyl,
  (iii) $C_5$–$C_{10}$ cycloalkyl, (iv) $C_7$–$C_{12}$ aralkyl, or
(v) phenyl optionally substituted by one, 2, or 3
(a) hydroxy,
(b) $C_1$–$C_3$ alkoxy,
(c) $C_1$–$C_3$ alkyl,
(d) trifluoromethyl,
(e) halo which is fluoro, chloro, or bromo, with the proviso that not more than two such substituents are other than alkyl, or wherein $R_{10}$ and $R_{11}$ are taken together with the nitrogen to form a saturated or unsaturated heterocyclic amine ring consisting of from 2 to 7 carbon atoms, inclusive, and zero, one, or 2 additional hetero atoms or hetero atom groups, with the proviso that said heterocyclic amine ring contains 4 to 8 atoms in the ring, said additional hetero atoms or hetero atom groups being selected from the group consisting of oxygen, nitrogen, sulfur, —SO—, and —$SO_2$— said heterocyclic amine ring being optionally substituted by one or 2 $C_1$–$C_4$ alkyl, $C_2$–$C_8$ alkylthiomethyl, or $C_2$–$C_8$ alkoxymethyl, $C_1$–$C_4$ hydroxyalkyl or phenyl;

wherein $R_1$ and $R_2$ are taken together and form a bivalent moiety which is:
(a) —$CH_2$—$(CH_2)_a$—$CH_2$— wherein the integer "a" is zero to 5;
(b) —$CH_2$—$(CH_2)_b$—X—$(CH_2)_c$—$CH_2$— wherein the integer "b" is zero and the integer "c" is zero, one, 2, or 3 or the integer "b" is one and the integer "c" is zero, one, or 2, and wherein x is oxa (—O—), thia (—S—), or —N($R_{10}$)— wherein $R_{10}$ is
(i) hydrogen,
(ii) $C_1$–$C_8$ alkyl,
(iii) $C_5$–$C_{10}$ cycloalkyl,
(iv) $C_7$–$C_{12}$ aralkyl, or
(v) phenyl optionally substituted by one, 2, or 3
(a) hydroxy,
(b) $C_1$–$C_3$ alkoxy,
(c) $C_1$–$C_3$ alkyl,
(d) trifluoromethyl,
(e) halo which is fluoro, chloro, or bromo, with the proviso that not more than two such substituents are other than alkyl;

wherein $R_3$ is hydrogen, or $C_1$–$C_4$ alkoxy and $R_4$ is hydrogen or $C_1$–$C_4$ alkoxy, with the proviso that one of $R_3$ and $R_4$ is hydrogen only when the other is other than hydrogen; and wherein $R_8$ and $R_9$, being the same or different, are individually,
(i) hydrogen,
(ii) $C_1$–$C_8$ alkyl,
(iii) $C_5$–$C_{10}$ cycloalkyl,
(iv) $C_7$–$C_{12}$ aralkyl, or
(v) phenyl optionally substituted by one, 2, or 3
(a) hydroxy,
(b) $C_1$–$C_3$ alkoxy,
(c) $C_1$–$C_3$ alkyl,
(d) trifluoromethyl,
(e) halo which is fluoro, chloro, or bromo, with the proviso that not more than two such substituents are other than alkyl, or wherein $R_8$ and $R_9$ are taken together with the nitrogen to form a saturated or unsaturated heterocyclic amine ring consisting of from 2 to 7 carbon atoms, inclusive, and zero, one, or 2 additional hetero atoms or hetero atom groups, with the proviso that said heterocyclic amine ring contains 4 to 8 atoms in the ring, said additional hetero atoms or hetero atom groups being selected from the group consisting of oxygen, nitrogen, sulfur, —SO—, and —$SO_2$— said heterocyclic amine ring being optionally substituted by one or 2 $C_1$–$C_4$ alkyl, $C_2$–$C_8$ alkylthiomethyl, or $C_2$–$C_8$ alkoxymethyl, $C_1$–$C_4$ hydroxyalkyl or phenyl.

2. An antiatherosclerotic compound according to claim 1 of Formula I.

3. An antiatherosclerotic compound according to claim 2 selected from the group consisting of:
(a) 5,9-Dimethoxy-2-(1-pyrrolidinyl)-4H-furo[3,2-g][1,3]benzoxazin-4-one;
(b) 5,9-Dimethoxy-2-(4-morpholinyl)-4H-furo[3,2-g][1,3]benzoxazin-4-one;
(c) 5,9-Dimethoxy-2-K(N,N-dimethylamino)-4H-furo[3,2-g][1,3]benzoxazin-4-one;
(d) 2-[2-(Hydroxymethyl)-1-pyrrolidinyl]-5,9-dimethoxy-4H-furo[3,2-g][1,3]benzoxazin-4-one;
(e) 5,9-Dimethoxy-2-(4-methyl-1-piperazinyl)-4H-furo[3,2-g]benzoxazin-4-one;
(f) 5,9-Dimethoxy-2-(tetrahydro-4H-1,4-thiazin-4-yl)-4H-furo[3,2-g]1,3]benzoxazin-4-one;
(g) 2-[[2-(Diethylamino)-ethyl]ethylamino]-5,9-dimethoxy-4H-furo[3,2-g][1,3]benzoxazin-4-one;
(h) 5,9-Dimethoxy-2-(3-thiazolidinyl)-4H-furo[3,2-g][1,3]benzoxazin-4-one;
(i) 2-[[(2S)-6,6-Dimethyl-(bicyclo[3.1.1]hept-2-yl)methyl]amino]-5,9-dimethoxy-4H-furo[3,2-g][1,3]benzoxazin-4-one; and
(j) 2-(2,6-Dimethyl-4-morpholinyl)-5,9-dimethoxy-4H-furo[3,2-g][1,3]benzoxazin-4-one.

4. An antiatherosclerotic compound according to claim 1 of Formula II.

5. An antiatherosclerotic compound according to claim 4 selected from the group consisting of:
(a) 5,9-Dimethoxy-4H-furo[3,2-g][1,3]benzoxazine-2,4-dione;
(b) 2′,3′,5′,6′-Tetrahydro-5,9-dimethoxy-spiro[2H-furo[3,2-g][1,3]benzoxazine-2,4′-[4H]thiopyran]-4(3H)-one;
(c) 5′,9′-Dimethoxy-spiro[cyclohexane-1,2′-[2H]furo[3,2-g][1,3]benzoxazin-4′(3′H)-one;
(d) 2,2-Diethyl-2,3-dihydro-5,9-dimethoxy-4H-furo[3,2-g][1,3]benzoxazin-4-one; and
(e) 2,3-Dihydro-5,9-dimethoxy-2-methyl-2-[(methylthio)methyl]-4H-furo[3,2-g][1,3]benzoxazin-4-one.

6. An antiatherosclerotic compound according to claim 1 of Formula III.

7. 4,9-Dimethoxyfuro[3,2-g]phthalazin-5(6H)-one, an antiatherosclerotic compound according to claim 6.

* * * * *